US012753140B2

(12) United States Patent
Harrison

(10) Patent No.: US 12,753,140 B2
(45) Date of Patent: Oct. 6, 2026

(54) CHLORINATED FLUOROAROMATICS AND METHODS OF USING SAME

(71) Applicant: 3M INNOVATIVE PROPERTIES COMPANY, St. Paul, MN (US)

(72) Inventor: Daniel J. Harrison, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 783 days.

(21) Appl. No.: 17/787,440

(22) PCT Filed: Dec. 28, 2020

(86) PCT No.: PCT/IB2020/062493
§ 371 (c)(1),
(2) Date: Jun. 20, 2022

(87) PCT Pub. No.: WO2021/137137
PCT Pub. Date: Jul. 8, 2021

(65) Prior Publication Data

US 2023/0339834 A1 Oct. 26, 2023

Related U.S. Application Data

(60) Provisional application No. 62/955,594, filed on Dec. 31, 2019.

(51) Int. Cl.

| | |
|---|---|
| ***C07C 43/225*** | (2006.01) |
| ***C09K 5/10*** | (2006.01) |
| ***H01B 3/24*** | (2006.01) |
| ***H01M 10/0525*** | (2010.01) |
| ***H01M 10/613*** | (2014.01) |
| ***H01M 10/6567*** | (2014.01) |

(52) U.S. Cl.
CPC .............. *C07C 43/225* (2013.01); *C09K 5/10* (2013.01); *H01B 3/24* (2013.01); *H01M 10/0525* (2013.01); *H01M 10/613* (2015.04); *H01M 10/6567* (2015.04)

(58) Field of Classification Search
CPC ...................... C07C 43/225; C07C 323/01–09
See application file for complete search history.

(56) References Cited

U.S. PATENT DOCUMENTS

| | | | | |
|---|---|---|---|---|
| 2,477,342 | A | 7/1949 | Mcbee et al. | |
| 2,516,403 | A | 7/1950 | McBee | |
| 3,513,172 | A | 5/1970 | Brokke | |
| 4,020,112 | A | 4/1977 | Boswell | |
| 4,126,623 | A * | 11/1978 | Piccardi | C07C 17/25 568/663 |
| 2016/0152636 | A1* | 6/2016 | Fujimori | C07D 319/06 544/335 |

FOREIGN PATENT DOCUMENTS

| | | | | |
|---|---|---|---|---|
| CN | 107235875 | | 6/2017 | |
| DE | 3908450 | | 3/1989 | |
| EP | 1080722 | A1 * | 3/2001 | A61P 31/10 |
| JP | 2006335677 | A * | 12/2006 | |
| WO | 2019067394 | A1 | 4/2019 | |
| WO | 2020250104 | A1 | 12/2020 | |

OTHER PUBLICATIONS

Betterley, N. M. et al. "Electrophilic Difluoro(phenylthio)methylation: Generation, Stability, and Reactivity of α-Fluorocarbocations" Org. Lett., vol. 15, No. 22, 2013 (Year: 2013).*

Dai, "Construction of β-Trifluoromethyl Enol Ether via Base-Promoted C—O Coupling and Rearrangement of Hydrogen Atom", Journal of Organic Chemistry, Apr. 2017, vol. 82, No. 9, pp. 4721-4728, XP55791978A.

Fang, "AIBN-initiated radical addition of gem-difluorinated alkyl iodides to alkynes and the Pd-catalyzed Sonogashira coupling reaction of E-phenyl difluoromethylene vinylic iodides with terminal alkynes", Tetrahedron, Oct. 2007, vol. 63, No. 43, pp. 10684-10692, XP22240257A.

Furin, "Synthesis of Partially Fluorinated Organic Compounds from Perfluoro-2-methyl-2-pentene and Phenol Derivatives", Russian Journal of General Chemistry, 2005, vol. 75, No. 3, pp. 394-401, XP19301026A.

Harada, "Electronic effect of aryl groups on the Z/E ratio of 1-aryloxypentafluoropropenes", Journal of Fluorine Chemistry, Jan. 1978, vol. 11, No. 1, pp. 87-92, XP002119612.

International Search Report for PCT International Application No. PCT/IB2020/062493, mailed on Apr. 13, 2021, 5 pages.

Makarov, "Hexafluoropropene trimer. Synthesis and properties of functional derivatives", Journal of Fluorine Chemistry, Oct. 1977, vol. 10, No. 4, pp. 323-327.

Maruta, "Mode of the nucleophilic reaction of F-2,4-dimethyl-3-heptene and phenol", Journal of Fluorine Chemistry, May 1979, vol. 13, No. 5, pp. 421-429.

(Continued)

*Primary Examiner* — Medhanit W Bahta
(74) *Attorney, Agent, or Firm* — Jeffrey M Olofson

(57) ABSTRACT

A chlorinated fluoroaromatic compound having structural formula (I): where G is an oxygen or sulfur atom; each $R^1$ is, independently, a fluoroalkenyl group having 2 to 10 carbon atoms and optionally comprises one or more catenated heteroatoms; each $R^2$ is, independently, (i) a hydrogen atom or a fluorine atom; or (ii) a fluoroalkyl group or a fluoroalkenyl group having 1 to 9 carbon atoms and optionally comprises one or more catenated heteroatoms; $R^3$ is a hydrogen atom or a fluorine atom; a is 1-3; x is 1 or 2; y is 1-4; and z=6-a-x-y.

I

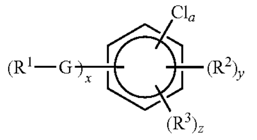

11 Claims, No Drawings

(56) References Cited

OTHER PUBLICATIONS

Nobuo, “The Reactions of the Dimers of Hexafluoropropene with O-Nucleophiles”, Bulletin of the Chemical Society of Japan, 1976, vol. 49, No. 2, pp. 502-505.
Xiao, “The chemistry of tetrafluoroallene. Nucleophilic addition reactions with phenols and amines”, Journal of Fluorine Chemistry, Oct. 2003, Vo. 123, No. 2, pp. 189-195, XP4463215A.
Yagupol’Skii, “Arylperfluoropropenyl Sulfides and Sulfones”, Institute of Organic Chemistry, Academy of Sciences of the UkrSSR, Jul. 1968, vol. 38, No. 7, pp. 1503-1509, XP9526693A.
Hock, et al., Chemical Communications, May 19, 2017, 207, vol. 53, pp. 6577-6580, Enabling Iron Catalyzed Doyle-Kirmse.
Zhang et al., Nature Communications 2019, Jan. 17, 2019, vol. 10:284, pp. 1-9, Use of Trifluoroacetaldehyde.

* cited by examiner

CHLORINATED FLUOROAROMATICS AND METHODS OF USING SAME

CROSS REFERENCE TO RELATED APPLICATIONS

This application is a national stage filing under 35 U.S.C. 371 of PCT/IB2020/062493, filed Dec. 28, 2020, which claims the benefit of U.S. Provisional Application No. 62/955,594, filed Dec. 31, 2019, the disclosure of which is incorporated by reference in its/their entirety herein.

FIELD

The present disclosure relates to chlorinated fluoroaromatic compounds and methods of making and using the same, and to working fluids that include the same.

BACKGROUND

Various fluoroaromatic compounds are described in, for example, "The Reactions of the Dimers of Hexafluoropropene with O-Nucleophiles", Nobuo, I.; Nagashima, A. *Bulletin of the Chemical Society of Japan* 1976, 49, 502-505; "Mode of the nucleophilic reaction of F-2,4-dimethyl-3-heptene and phenol", Maruta, M.; Ishikawa, N. *Journal of Fluorine Chemistry* 1979, 13, 421-429. Various chlorine containing fluoroaromatic compounds are described in, for example, "Synthesis of partially fluorinated organic compounds from perfluoro-2-methyl-2-pentene and phenol derivatives", Furin, G. G.; Zhuzhgov, E. L.; Chi, K.-V., Kim, N.-A. *Russian Journal of General Chemistry* 2005, 75, 394-401; and Takeshi, M.; Kazuyuki, O.; Yasunori, O.; Toshiya, I. Perfluoroalkenyl Derivative. Japanese Patent Application 2006335677, Dec. 14, 2006.

SUMMARY

In some embodiments, a chlorinated fluoroaromatic compound having structural formula (I) is provided.

I

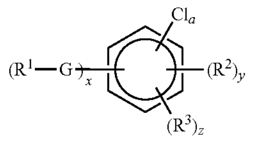

where G is an oxygen or sulfur atom;

each $R^1$ is, independently, a fluoroalkenyl group having 2 to 10 carbon atoms and optionally comprises one or more catenated heteroatoms;

each $R^2$ is, independently, (i) a hydrogen atom or a fluorine atom; or (ii) a fluoroalkyl group or a fluoroalkenyl group having 1 to 9 carbon atoms and optionally comprises one or more catenated heteroatoms;

$R^3$ is a hydrogen atom or a fluorine atom;

a is 1-3;

x is 1 or 2;

y is 1-4; and z=6-a-x-y.

The above summary of the present disclosure is not intended to describe each embodiment of the present disclosure. The details of one or more embodiments of the disclosure are also set forth in the description below. Other features, objects, and advantages of the disclosure will be apparent from the description and from the claims.

DETAILED DESCRIPTION

In view of an increasing demand for environmentally friendly chemical compounds (due to environmental concern as well as industry regulation), it is recognized that there exists an ongoing need for new working fluids that provide reductions in environmental impact (e.g., exhibit low global warming potentials (GWPs)). In addition to environmental concerns, such compounds should meet the performance requirements (e.g., nonflammability, solvency, stability, low toxicity, low dielectric constants, and wide operating temperature range) of a variety of applications (e.g., heat transfer, immersion cooling, solvent cleaning, and deposition coating solvents), and be manufactured cost-effectively. More specifically, there is a need for non-flammable, high-boiling working fluids for high temperature applications (such as those discussed below) which possess wide liquid ranges (e.g., <−50 to >180° C. at 760 Torr), low dielectric constants (e.g., <3 at 1 kHz), and very low global warming potentials (GWPs) (e.g., <100, as defined below).

Generally, the present disclosure relates to certain chlorinated fluoroaromatic compounds that are particularly useful as high boiling heat transfer fluids, dielectric fluids, immersion cooling fluids, or fluids for converting thermal energy into mechanical energy. Notably, the compounds of the present disclosure have significantly lower GWPs compared to related working fluids used in the industry (e.g., perfluorocarbons (PFCs), perfluoropolyethers (PFPEs) and hydrofluorocarbons (HFCs)). Furthermore, certain of the compounds exhibit non-flammability, low ozone depletion potential (ODP), and low toxicity.

Still further, the compounds of the present disclosure exhibit surprisingly favorable dielectric properties (i.e., low dielectric constants and high dielectric strengths) and high boiling points. Regarding the dielectric properties, it was discovered that the preferred embodiments exhibit dielectric constants less than 3 and dielectric strengths greater than 40 kV (2.5 mm gap), rendering the compounds conducive to immersion cooling applications in which electronic components are in direct contact with the working fluid.

It should be emphasized that the combination of low GWPs and favorable dielectric properties exhibited by the compounds of the present disclosure is surprising for high boiling fluorinated fluids used in the industry. For example, perfluoropolyethers (PFPEs) with boiling points in the ~130-200° C. range generally have excellent dielectric properties (dielectric constant≈1.9, dielectric strength≈40 kV) but also very high GWPs (~10,000). Conversely, hydrofluoroethers (HFEs) with boiling points in the ~130-170° C. range generally have lower GWPs than PFPEs (<500) but higher dielectric constants and lower dielectric strengths (≥5.8 and <30 kV, respectively). Thus, the chlorinated aromatics described here offer much lower GWPs and slightly higher dielectric strengths than PFPEs. Similarly, the chlorinated aromatics have lower GWPs, lower dielectric constants and higher dielectric strengths than HFEs.

Regarding the operating temperature range, it was discovered that certain of the chlorinated fluoroaromatic compounds have boiling points significantly higher than their non-chlorinated analogs (by >20° C.) and, in some embodiments, have boiling points greater than 190° C. and excellent thermal stability. Thus, these compounds are especially useful in high-temperature working fluids applications. Finally, certain of the compounds of the present disclosure can be manufactured cost-effectively due in part to the relatively low expense of the raw/starting materials.

As used herein, "catenated heteroatom" means an atom other than carbon (e.g., oxygen, nitrogen, or sulfur) that is bonded to at least two carbon atoms in a carbon chain (linear or branched or within a ring) so as to form a carbon-heteroatom-carbon linkage.

As used herein, "fluoro-" (e.g., in reference to a group or moiety, such as in the case of "fluoroalkene" or "fluoroalkenyl" or "fluoroalkane" or "fluoroalkyl" or "fluorocarbon") or "fluorinated" means (i) partially fluorinated such that there is at least one carbon-bonded hydrogen atom in addition to carbon-fluorine bond(s), or (ii) perfluorinated.

As used herein, "perfluoro-" (e.g., in reference to a group or moiety, such as in the case of "fluoroalkene" or "fluoroalkenyl" or "fluoroalkane" or "fluoroalkyl" or "fluorocarbon") or "perfluorinated" means completely fluorinated such that, except as may be otherwise indicated, there are no carbon-bonded hydrogen atoms replaceable with fluorine.

As used herein, "alkyl" means a molecular fragment comprised of a valence-saturated carbon-based skeleton (i.e., derived from an alkane), which may be linear, branched or cyclic.

As used herein, "alkenyl" means a molecular fragment comprised of a carbon-base skeleton, which contains at least one carbon-carbon double bond (i.e., derived from alkene, diene, etc.); alkenyl fragments may be linear, branched or cyclic.

As used herein, "fluoroaromatic" or "fluoroaromatic compound" refers to a compound having an aromatic moiety (i.e., a planar ring structure satisfying Hülckel's 4n+2 Rule; e.g., benzene and pyridine derivatives), which also contains carbon-fluorine bonds. The aromatic ring may be directly fluorinated (i.e., with aryl carbon-fluorine bonds; e.g., pentafluorophenol derivatives), with group(s) attached to the aromatic ring that also contain carbon-fluorine bond(s) (e.g., fluoroalkyl, fluoroalkenyl, and derivatives thereof containing catenated heteroatom(s)). Alternatively, the aromatic ring may be non-fluorinated (i.e., without aryl carbon-fluorine bonds; e.g., phenol derivatives), with group(s) attached to the aromatic ring that contain carbon-fluorine bond(s) (e.g., fluoroalkyl, fluoroalkenyl, and derivatives thereof containing catenated heteroatom(s)).

As used herein, "chlorinated fluoroaromatic" refers to compounds satisfying the definitions above for "fluoroaromatics" and, further, having one or more chlorine atoms attached to the aromatic ring.

As used herein, the singular forms "a", "an", and "the" include plural referents unless the content clearly dictates otherwise. As used in this specification and the appended embodiments, the term "or" is generally employed in its sense including "and/or" unless the content clearly dictates otherwise.

As used herein, the recitation of numerical ranges by endpoints includes all numbers subsumed within that range (e.g., 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should be construed in light of the number of reported significant digits and by applying ordinary rounding techniques.

In some embodiments, the present disclosure is directed to chlorinated fluoroaromatic compounds represented by the following structural formula (I):

I

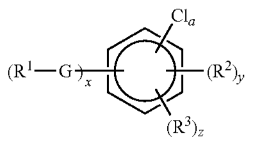

where G is an oxygen or sulfur atom;

each $R^1$ is, independently, a fluoroalkenyl group having 2 to 10, 3 to 9, or 4 to 9 carbon atoms and optionally comprises one or more catenated heteroatoms;

each $R^2$ is, independently, (i) a hydrogen atom or a fluorine atom; or (ii) a fluoroalkyl group or a fluoroalkenyl group having 1 to 9 carbon atoms and optionally comprises one or more catenated heteroatoms;

each $R^3$ is a hydrogen atom or a fluorine atom;

a is 1-3, 1-2, or 1;

x is 1 or 2 or 1;

y is 1-4, 1-3, or 1-2; and z=6-a-x-y.

In some embodiments, either or both of $R^1$ and $R^2$ (when $R^2$ is a fluoroalkyl or a fluoroalkenyl group) may be perfluorinated.

In some embodiments, the present disclosure is directed to chlorinated fluoroaromatic compounds represented by the following structural formula (II):

II

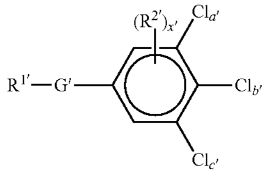

where G' is an oxygen or sulfur atom;

$R^{1'}$ is a fluoroalkenyl group having 2 to 10, 3 to 9, or 4 to 9 carbon atoms and optionally comprises one or more catenated heteroatoms;

each $R^{2'}$ is, independently, (i) a hydrogen atom or a fluorine atom; or (ii) a fluoroalkyl group or a fluoroalkenyl group having 1 to 9 carbon atoms and optionally comprises one or more catenated heteroatoms;

x' is 2-4 or 2-3; and a', b' and c' are, independently, 0 or 1.

In some embodiments, either or both of $R^{1'}$ and $R^{2'}$ (when $R^{2'}$ is a fluoroalkyl or a fluoroalkenyl group) may be perfluorinated.

In some embodiments, the fluorine content in the chlorinated fluoroaromatic compounds of the present disclosure may be sufficient to make the compounds non-flammable according to ASTM D-3278-96 e-1 test method ("Flash Point of Liquids by Small Scale Closed Cup Apparatus").

In various embodiments, representative examples of the compounds of general formula I or II include the following:

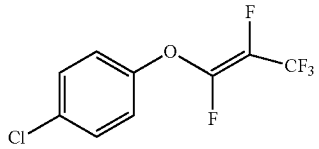
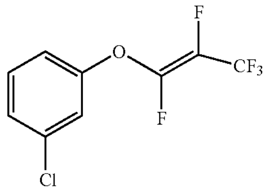
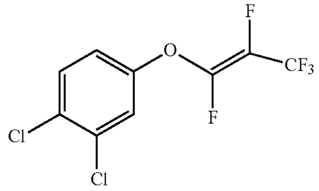
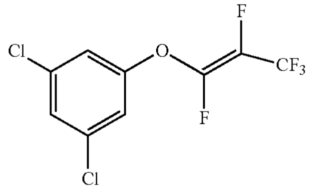
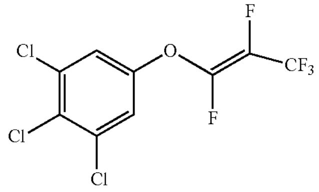
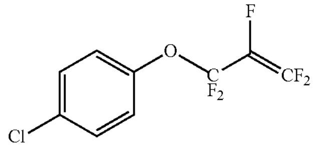
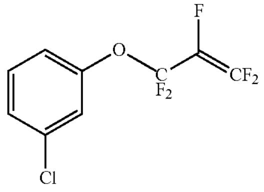
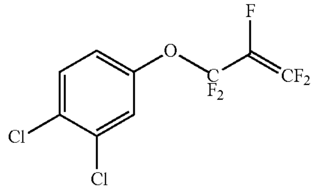
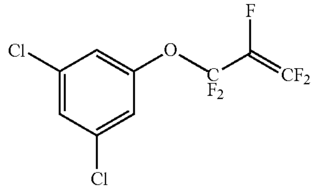
-continued
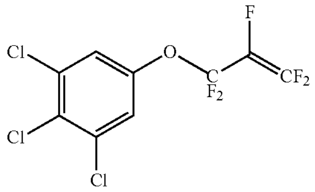
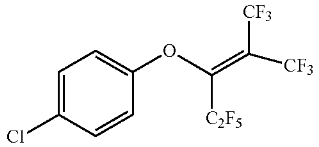
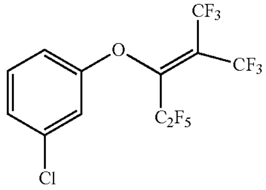
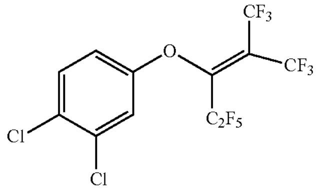
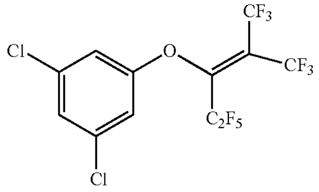
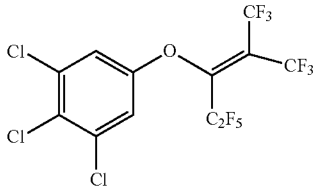
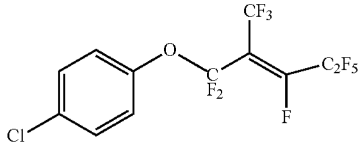
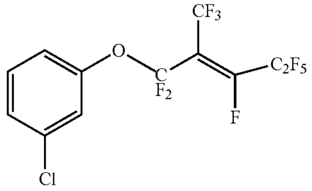
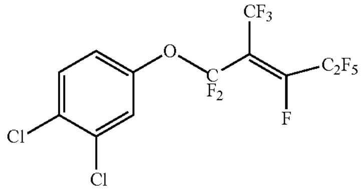

-continued
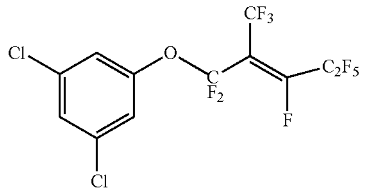
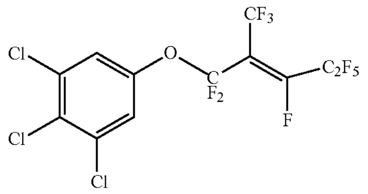
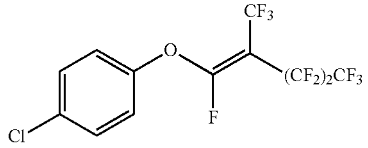
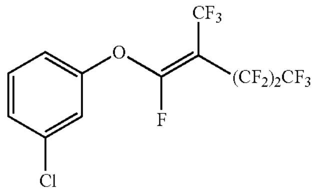
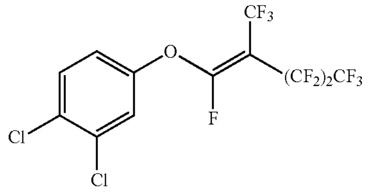
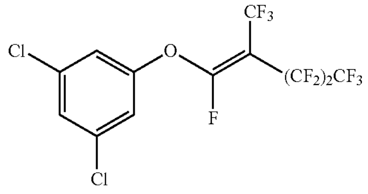
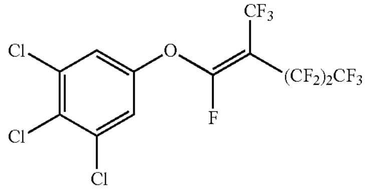
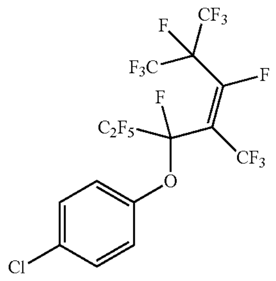
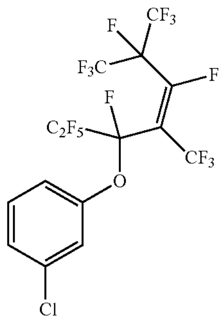
-continued
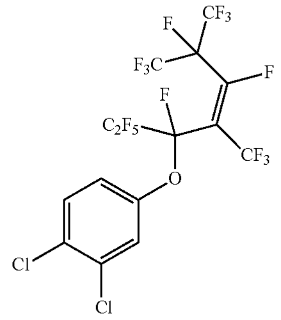
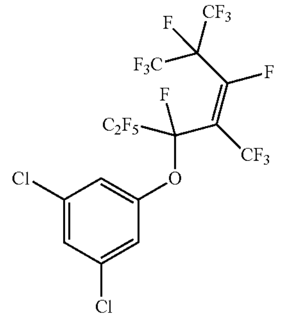
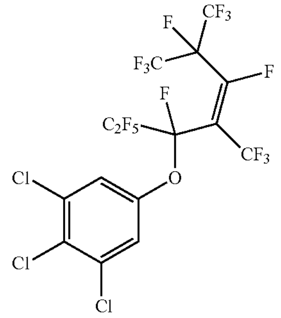
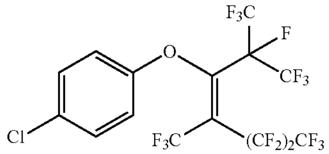
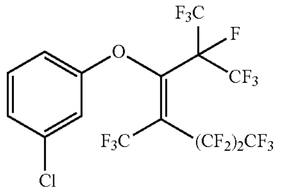
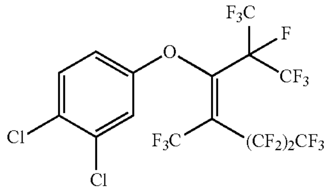
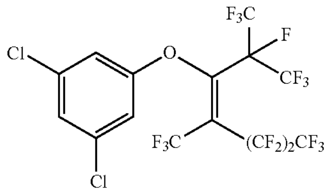

-continued
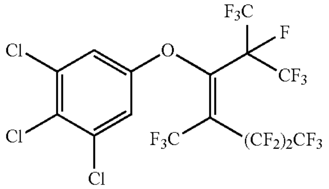
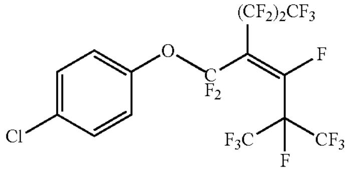
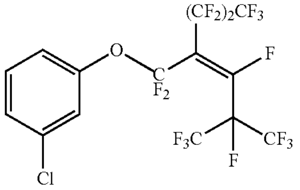
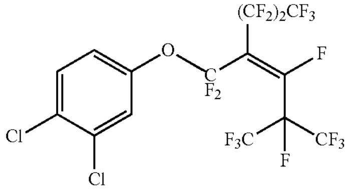
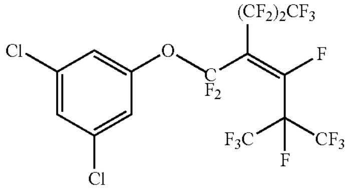
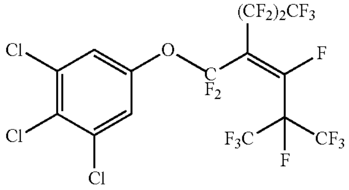
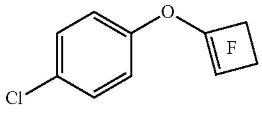
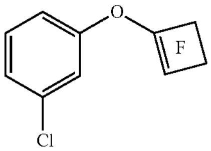
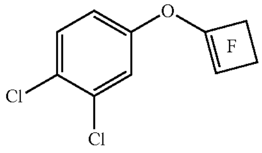
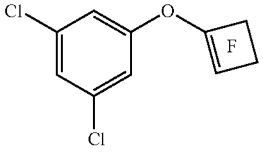
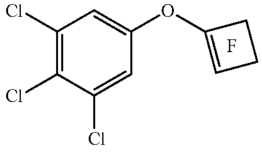
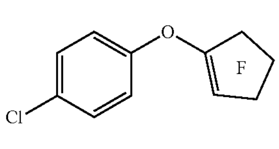
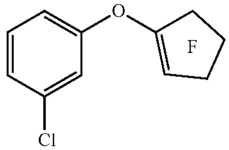
-continued
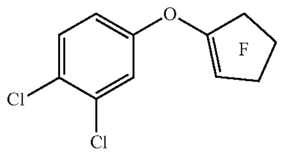
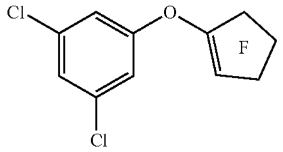
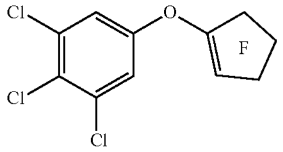
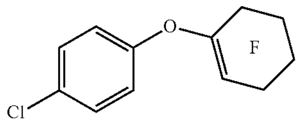
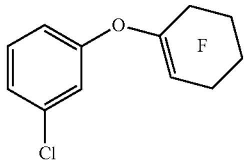
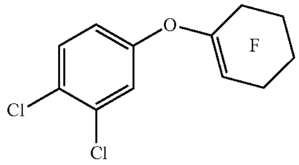
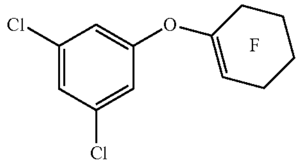
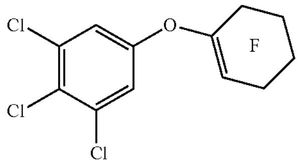
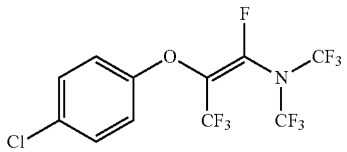
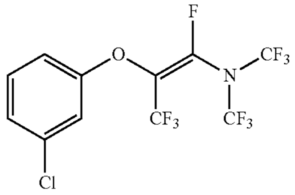

11
-continued
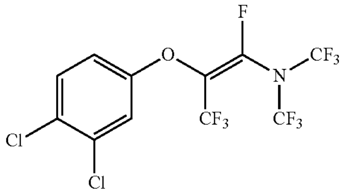
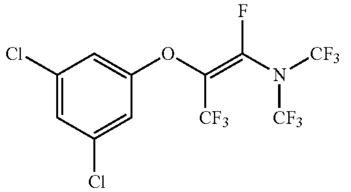
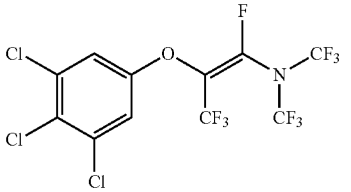
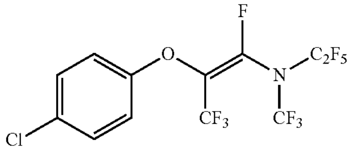
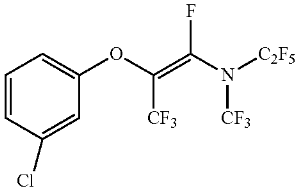
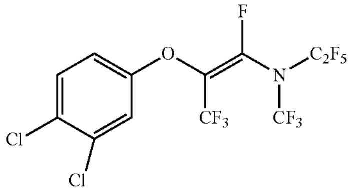
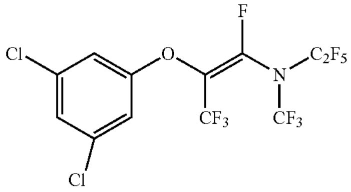
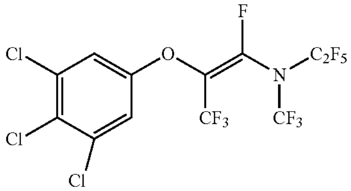
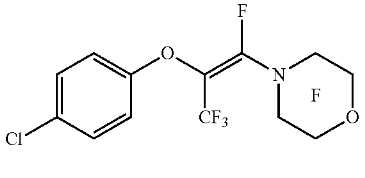
12
-continued
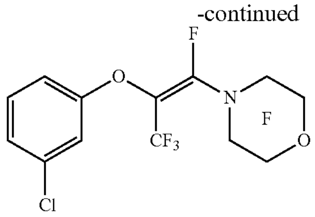
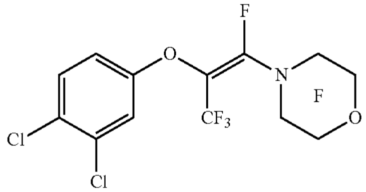
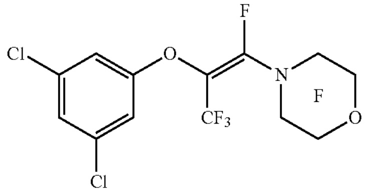
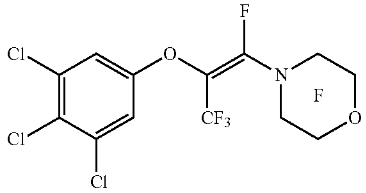
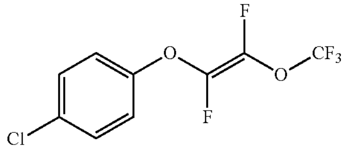
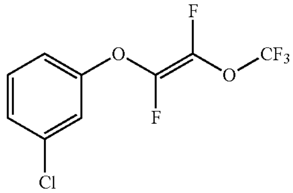
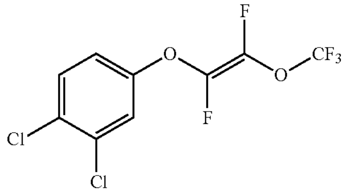
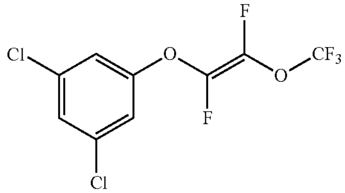
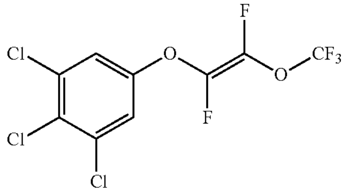

-continued

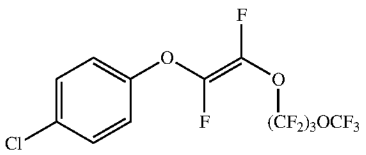

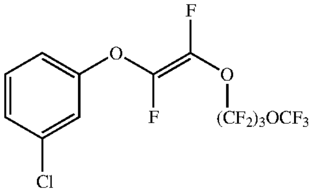

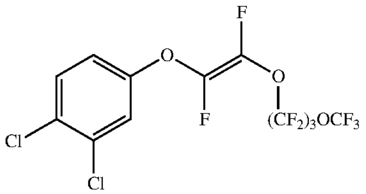

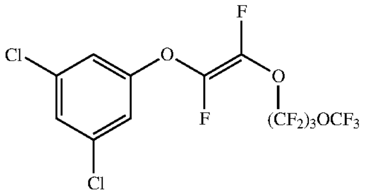

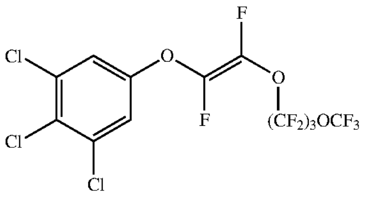

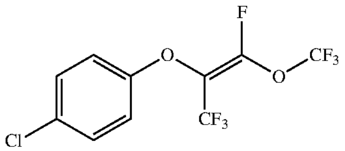

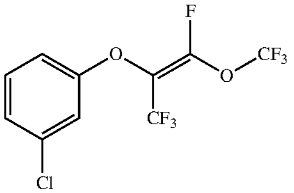

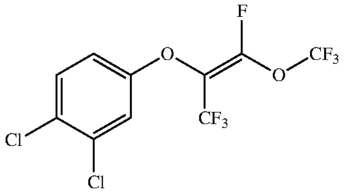

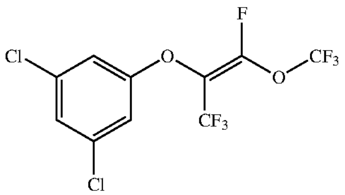

-continued

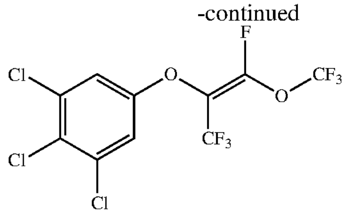

For purposes of the present disclosure, it is to be appreciated that any of the chlorinated fluoroaromatic compounds may include the E isomer, the Z isomer, or a mixture of the E and Z isomers, irrespective of what is depicted in any of the general formulas or chemical structures.

In some embodiments, the chlorinated fluoroaromatic compounds of the present disclosure may be useful over a broad operating temperature range. In this regard, in some embodiments, the chlorinated fluoroaromatics of the present disclosure may have a boiling point of not less than 220, 210, 200, 190, or 180 degrees Celsius.

In some embodiments, the chlorinated fluoroaromatic compounds of the present disclosure may be hydrophobic, relatively chemically unreactive, and thermally stable. The chlorinated fluoroaromatic compounds may have a low environmental impact. In this regard, the chlorinated fluoroaromatic compounds of the present disclosure may have a global warming potential (GWP) of less than 300, 200, 100, 50, 10, or less than 1. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of $CO_2$ over a specified integration time horizon (ITH).

$$GWP_i(t') = \frac{\int_0^{ITH} a_i[C(t)]dt}{\int_0^{ITH} a_{CO2}[C_{CO2}(t)]dt} = \frac{\int_0^{ITH} a_i C_{oi} e^{-t/\tau_i} dt}{\int_0^{ITH} a_{CO2}[C_{CO2}(t)]dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, τ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of $CO_2$ over that same time interval incorporates a more complex model for the exchange and removal of $CO_2$ from the atmosphere (the Bern carbon cycle model).

In some embodiments, the chlorinated fluoroaromatics of the present disclosure can be prepared by nucleophilic displacement of a fluoride ion from a fluoroalkene by a chlorophenolate ion (e.g., 4-chlorophenolate or 3,5-dichlorophenolate), using procedures adapted from the prior art. The chlorophenolate species may be a pre-formed alkali metal salt (e.g., sodium or potassium chlorophenolate).

Alternatively, chlorophenolate may be formed in the reaction medium from the parent chlorophenol in the presence of a Brønsted base; suitable bases include amines (e.g., triethylamine), alkali metal carbonates (e.g., sodium or potassium carbonate) or alkali metal hydroxides (e.g., sodium or potassium hydroxide). Suitable media for these reactions includes organic solvents such as N,N-dimethylformamide, acetone and tetrahydrofuran.

In some embodiments, the present disclosure is further directed to working fluids that include one or more of the above-described chlorinated fluoroaromatic compounds as a major component. For example, the working fluids may include at least 25%, at least 50%, at least 70%, at least 80%, at least 90%, at least 95%, or at least 99% by weight of the above-described chlorinated fluoroaromatic compounds, based on the total weight of the working fluid. In addition to the chlorinated fluoroaromatic compounds, the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, hydrochlorocarbons, hydrochlorofluorocarbons, hydrofluorocarbons, hydrochloroolefins, hydrochlorofluoroolefins, hydrofluoroethers, sulfones, or mixtures thereof, based on the total weight of the working fluid. Such additional components can be chosen to modify or enhance the properties of a composition for a particular use.

In some embodiments, the chlorinated fluoroaromatics of the present disclosure (or working heat transfer fluids containing the same) can be used in various applications as heat transfer agents (e.g., for the cooling or heating of integrated circuit tools in the semiconductor industry, including tools such as dry etchers, integrated circuit testers, photolithography exposure tools (steppers), ashers, chemical vapor deposition equipment, automated test equipment (probers), physical vapor deposition equipment (e.g. sputterers), and vapor phase soldering fluids, and thermal shock fluids).

In some embodiments, the present disclosure is further directed to an apparatus for heat transfer that includes a device and a mechanism for transferring heat to or from the device. The mechanism for transferring heat may include a heat transfer or working fluid that includes one or more chlorinated fluoroaromatics of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, heat exchangers, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility requires that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner, and it should have a low pour point and low viscosity to maintain fluidity during low temperature operation.

The provided apparatus may include a mechanism for transferring heat. The mechanism may include a heat transfer fluid. The heat transfer fluid may include one or more chlorinated fluoroaromatics of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature-controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 220° C.

Heat can be transferred by placing the heat transfer mechanism in thermal communication with the device. The heat transfer mechanism, when placed in thermal communication with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath.

In some embodiments, the present disclosure is directed to a thermal management system for an electrochemical cell pack (e.g., lithium-ion battery pack). The system may include an electrochemical cell pack and a working fluid in thermal communication with the battery pack. The working fluid may include one or more chlorinated fluoroaromatics of the present disclosure.

Electrochemical cells (e.g., lithium-ion batteries) are in widespread use worldwide in a vast array of electronic and electric devices ranging from hybrid and electric vehicles to power tools, portable computers, and mobile devices. While generally safe and reliable energy storage devices, lithium-ion batteries are subject to catastrophic failure known as thermal runaway under certain conditions. Thermal runaway is a series of internal exothermic reactions that are triggered by heat. The creation of excessive heat can be from electrical over-charge, thermal over-heat, or from an internal electrical short. Internal shorts are typically caused by manufacturing defects or impurities, dendritic lithium formation and mechanical damage. While there is typically protective circuitry in the charging devices and in the battery packs that will disable the battery in the event of overcharging or overheating, it cannot protect the battery from internal shorts caused by internal defects or mechanical damage.

A thermal management system for lithium-ion battery packs is often required to maximize the cycle life of lithium-ion batteries. This type of system maintains uniform temperatures of each cell within a battery pack. High temperatures can increase the capacity fade rate and impedance of lithium-ion batteries while decreasing their lifespan. Ideally, each individual cell within a battery pack will be at the same ambient temperature.

Direct contact fluid immersion of batteries can mitigate low probability, but catastrophic, thermal runaway events while also providing necessary ongoing thermal management for the efficient normal operation of the lithium-ion battery packs. This type of application provides thermal management when the fluid is used with a heat exchange system to maintain a desirable operational temperature range. However, in the event of mechanical damage or an internal short of any of the lithium-ion cells, the fluid would also prevent propagation or cascading of the thermal runaway event to adjacent cells in the pack via evaporative cooling, thus significantly mitigating the risk of a catastrophic thermal runaway event involving multiple cells. As with immersion cooling of electronics described above, immersion cooling and thermal management of batteries can be achieved using a system designed for single phase or two-phase immersion cooling and the fluid requirements for battery cooling are similar to those described above for electronics. In either scenario, the fluids are disposed in thermal communication with the batteries to maintain, increase, or decrease the temperature of the batteries (i.e., heat may be transferred to or from the batteries via the fluid).

Direct contact fluid immersion technology has been shown to be useful for thermal management of batteries and for providing thermal runaway protection, but there is still a need for improved fluids that can provide better chemical stability and system longevity, while addressing environmental concerns such as high GWP. Hydrofluoroethers and perfluoroketones are two examples of chemistries that have shown utility in direct contact fluid immersion heat transfer applications for thermal management and thermal runaway protection of batteries, while also providing acceptable global warming potentials. These applications place stringent performance requirements on the fluids employed, such as non-flammability, acceptable toxicity, small environmental footprint, high dielectric strength, low dielectric constant, high volume resistivity, stability, materials compatibility, and good thermal properties to maintain high volume resistivity over long periods. In some embodiments, the present disclosure applies to a direct contact fluid immersion thermal management system for an electrochemical cell pack. The system may include an electrochemical cell pack and a working fluid in thermal communication with the pack. The working fluid may include one or more of the chlorinated fluoroaromatics of the present disclosure.

In some embodiment, the present disclosure describes is directed to use of one or more of the chlorinated fluoroaromatics (or chlorinated fluoroaromatic containing working fluids) as single-phase immersion cooling fluids for electronic devices (e.g., computer server). There is no phase change in single phase immersion. Instead, typically, the fluid warms and cools as it flows or is pumped through the electronic device and a heat exchanger, respectively, thereby transferring heat away from the electronic device.

In some embodiments, the present disclosure may be directed to an immersion cooling system which operates by single-phase immersion cooling. Generally, the single phase immersion cooling system may include a heat generating component (e.g., computer server) disposed within the interior space of a housing such that it is at least partially immersed (and up to fully immersed) in the liquid phase of a working fluid. The single-phase system may further include a pump and a heat exchanger, the pump operating to move the working fluid to and from the heat generating electronic devices and the heat exchanger, and the heat exchanger operating to cool the working fluid. The heat exchanger may be disposed within or external to the housing.

EXAMPLES

Objects and advantages of this disclosure are further illustrated by the following comparative and illustrative examples. Unless otherwise noted, all parts, percentages, ratios, etc. in the examples and the rest of the specification are by weight, and all reagents used in the examples were obtained, or are available, from general chemical suppliers such as, for example, Sigma-Aldrich Corp. (Saint Louis, MO, US) or Oakwood Chemicals (Estill, SC, US). The following abbreviations are used herein: mL=milliliters, L=liters, mm=millimeters, min=minutes, h=hours, g=grams, mmol=millimoles, mol=moles, ° C.=degrees Celsius, bp=boiling point, GC=gas chromatography, FID=flame ionization detector, MS=mass spectrometry, i=iso and n=normal (referring to structural arrangements of carbon-based groups, as in iso- or normal-propyl), Ph=phenyl ($C_6H_5$), NMR=nuclear magnetic resonance, cSt=centi Stokes, KHz=kilohertz, kV=kilovolts.

Sample Preparation Procedures

Note that the procedures below for Examples 1 and 3 and Comparative Examples CE1 and CE3 yielded multiple isomers. The structures shown are the major isomers (>90 wt %).

Example 1

4-Cl($C_6H_4$)O($C_9F_{17}$): (E)-1-chloro-4-((1,1,1,2,2,3,5,6,7,7,7-undecafluoro-4,6-bis(trifluoromethyl)hept-4-en-3-yl)oxy)benzene+isomers

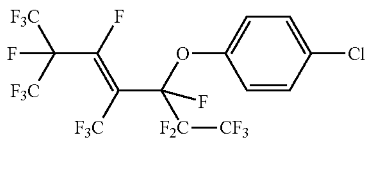 [SMILES: F/C(=C(/C(F)(F)F)C(F)(Oc1ccc(Cl)cc1)C(F)(F)C(F)(F)F)C(F)(C(F)(F)F)C(F)(F)F]

(E)-Perfluoro-2,4-dimethylhept-3-ene [(E)-CF(i-$C_3F_7$)=C($CF_3$)(n-$C_3F_7$)] was prepared according to procedure described in K. N. Makarov, et al., *Journal of Fluorine Chemistry* 1977, 10, 323-327. 4-Chlorophenol (84.7 g, 659 mmol), (E)-perfluoro-2,4-dimethylhept-3-ene (308 g, 684 mmol) and N,N-dimethylformamide (300 mL) were combined in a 1 L 3-neck flask, equipped with an addition funnel, temperature probe and magnetic stir bar. The slightly yellow biphasic mixture was cooled to ~12° C. in an ice bath. With vigorous stirring, triethylamine (66.7 g, 659 mmol) was added dropwise by addition funnel over 1 h, with the temperature between 10 and 15° C. The biphasic mixture (yellow top layer, faintly yellow bottom layer) was stirred at ambient temperature (21-23° C.) for 1 h 30 min. The layers were separated. The bottom (fluorocarbon) layer was washed with water (200 mL×3), dried over magnesium sulfate and filtered (clear, slightly yellow liquid). This material was purified by distillation under vacuum (bp≈80° C. at 5 Torr), followed by filtration through silica (20 g). The yield was 238 g (65%), with >99% purity for the combined 4-Cl($C_6H_4$)O($C_9F_{17}$) isomers, as established by GC-MS and NMR.

Example 2

4-Cl($C_6H_4$)O($C_6F_{11}$): 1-chloro-4-((1,1,1,4,4,5,5,5-octafluoro-2-(trifluoromethyl)pent-2-en-3-yl)oxy)benzene

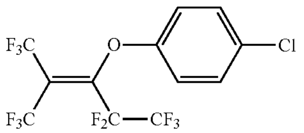

Acetone (250 mL), powdered potassium carbonate (~325 mesh, 150.2 g, 1087 mmol) and perfluoro-2-(methyl)pent-2-ene [CF($C_2F_5$)=C($CF_3$)$_2$] (250.4 g, 834.7 mmol) were combined (slightly yellow suspension) in a 1 L 3-neck flask, equipped with an addition funnel, temperature probe and magnetic stir bar. The mixture was cooled to ~2° C. in an ice bath. With vigorous stirring, a solution of 4-chlorophenol (107.2 g, 833.6 mmol) in acetone (50 mL) was added dropwise over 45 min, with the temperature between 0 and 5° C. The yellow suspension was stirred at ambient temperature (21-23° C.) for 1 h 40 min. The mixture was filtered; the solids were washed with acetone (50 mL×3) and these washings were collected with the rest of the yellow filtrate. The filtrate was concentrated under vacuum (~0.5-1.0 Torr) in a water bath kept between 12 and 20° C. (~350 mL of acetone was removed). The concentrated material was washed with water (200 mL×3), dried over magnesium sulfate and filtered (clear, yellow liquid). This material was purified by distillation under vacuum (bp≈61° C. at 6.4 Torr), followed by filtration through silica (10 g). The yield of 4-Cl($C_6H_4$)O($C_6F_{11}$) was 195 g (57%), with >99% purity, as established by GC-FID and GC-MS.

Example 3

3,5-$Cl_2$($C_6H_3$)O($C_9F_{17}$): (E)-1,3-dichloro-5-((1,1,1,2,2,3,5,6,7,7,7-undecafluoro-4,6-bis(trifluoromethyl)hept-4-en-3-yl)oxy)benzene+isomers

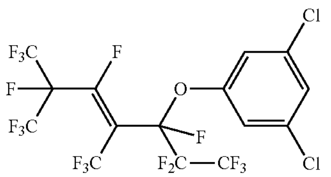 [SMILES: F/C(=C(/C(F)(F)F)C(F)(Oc1cc(Cl)cc(Cl)c1)C(F)(F)C(F)(F)F)C(F)(C(F)(F)F)C(F)(F)F]

3,5-Dichlorophenol (52.5 g, 322 mmol, 100 mass %), N,N-dimethylformamide (170 mL) and (E)-perfluoro-2,4-dimethylhept-3-ene [(E)-CF(i-$C_3F_7$)=C($CF_3$)(n-$C_3F_7$), prepared using the procedure referenced in Example 1] (146 g, 324 mmol) were combined in a 500 mL 3-neck flask, equipped with an addition funnel, temperature probe and magnetic stir bar under a nitrogen atmosphere. The biphasic, yellow-brown mixture was cooled to 5° C. in an ice bath. With vigorous stirring, triethylamine (33.0 g, 326 mmol) was added dropwise over 0.5 h, with the temperature between 5 and 7° C. After 10 min at 5-7° C., stirring was stopped and the layers were separated. The bottom layer (slightly yellow) was washed with hydrochloric acid (5 wt. %, 135 mL×2) and water (135 mL×2), dried over magnesium sulfate and filtered. This material was purified by distillation under vacuum (bp≈88° C. at 5.2 Torr). The yield was 109 g (57%), with >99% purity for the combined 3,5-$Cl_2$($C_6H_3$)O($C_9F_{17}$) isomers, as established by GC-FID and GC-MS.

Comparative Example CE1

PhO($C_9F_{17}$): (E)-((1,1,1,2,2,3,5,6,7,7,7-Undecafluoro-4,6-bis(trifluoromethyl)hept-4-en-3-yl)oxy)benzene+isomers

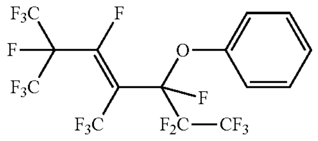 [SMILES: F/C(=C(/C(F)(F)F)C(F)(Oc1ccccc1)C(F)(F)C(F)(F)F)C(F)(C(F)(F)F)C(F)(F)F]

Under an atmosphere of nitrogen, triethylamine (210 g, 2080 mmol) was added dropwise by addition funnel, over 25 min, to a vigorously stirred biphasic mixture of phenol (193 g, 2050 mmol), N,N-dimethylformamide (1100 mL), and (E)-perfluoro-2,4-dimethylhept-3-ene [(E)-CF(i-$C_3F_7$)=C($CF_3$)(n-$C_3F_7$), prepared using the procedure referenced in Example 1] (923 g, 2050 mmol). The internal temperature was kept between 15 and 22° C. during the addition. The mixture was stirred at ambient temperature for 3 h. The layers were separated; the fluoro-organic layer (bottom) was washed with 5 wt % hydrochloric acid (1 L×2) and water (0.5 L×2), dried over magnesium sulfate, and filtered. The crude material was purified by vacuum distillation (bp~61° C. at 5.0 Torr). The yield was 924 g (86%), with >99% purity for the combined PhO($C_9F_{17}$) isomers, as established by GC-MS and NMR.

Comparative Example CE2

PhO($C_6F_{11}$): 3,3,3-trifluoro-1-(1,1,2,2,2-pentafluoroethyl)-2-(trifluoromethyl)prop-1-enoxy]benzene

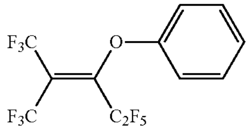

Under an atmosphere of nitrogen, triethylamine (120 mL, 861 mmol) was added dropwise via addition funnel to a vigorously stirred biphasic mixture of phenol (80 g, 850 mol), N,N-dimethylformamide (254 mL) and perfluoro-2-(methyl)pent-2-ene [$CF(C_2F_5)$=$C(CF_3)_2$] (280.6 g, 935.2 mmol). The internal temperature was kept between 20 and 40° C. during the addition. The mixture was stirred at ambient temperature (21-23° C.) for 1 h 15 min. The fluoro-organic phase (bottom) was separated, washed water (300 mL×3), dried over magnesium sulfate, and filtered. The crude material was purified by vacuum distillation (bp≈55° C. at 6.5 Torr) . . . . The yield of $PhO[C(C_2F_5)$=$C(CF_3)_2]$ was 655 g (83%), with 98% purity, as established by GC-MS and NMR.

Comparative Example CE3

4-$F(C_6H_4)O(C_9F_{17})$: (E)-1-fluoro-4-((1,1,1,2,2,3,5,6,7,7,7-undecafluoro-4,6-bis(trifluoromethyl)hept-4-en-3-yl)oxy)benzene+isomers

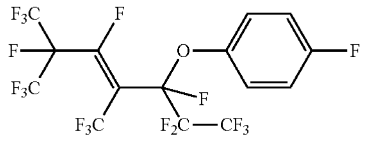 [SMILES: F/C(=C(/C(F)(F)F)C(F)(Oc1ccc(F)cc1)C(F)(F)C(F)(F)F)C(F)(C(F)(F)F)C(F)(F)F]

4-Fluorophenol (71.2 g, 635 mmol), (E)-perfluoro-2,4-dimethylhept-3-ene [(E)-$CF(i-C_3F_7)$=$C(CF_3)(n-C_3F_7)$, prepared using the procedure referenced in Example 1] (300.7 g, 668.1 mmol) and N,N-dimethylformamide (300 mL) were combined in a 1 L 3-neck flask, equipped with an addition funnel, temperature probe and magnetic stir bar. The slightly yellow biphasic mixture was cooled to ~12° C. in an ice bath. With vigorous stirring, triethylamine (64.4 g, 636 mmol) was added dropwise by addition funnel over 45 min, with the temperature between 10 and 15° C. The biphasic mixture (yellow top layer, faintly yellow bottom layer) was stirred at ambient temperature (21-23° C.) for 1 h 30 min. The layers were separated. The bottom (fluorocarbon) layer was washed with hydrochloric acid (5 wt. %) (200 mL×2) and water (100 mL×2), dried over magnesium sulfate and filtered (clear, colorless liquid). This material was purified by distillation under vacuum (bp≈66° C. at 5.1 Torr), followed by filtration through silica (15 g). The yield was 262 g (76%), with >99% purity for the combined 4-$F(C_6H_4)O(C_9F_{17})$ isomers, as established by GC-FID and GC-MS.

Test Methods

The boiling points reported in Table 1 were determined using the procedures outlined in ASTM E 1719-97 "Standard Test Method for Vapor Pressure of Liquids by Ebulliometry." First, vapor pressure was measured, and then the boiling point was calculated as described in section 10 of ASTM method E1719-97.

Dielectric constants were measured using an Alpha-A High Temperature Broadband Dielectric Spectrometer (Novocontrol Technologies, Montabaur, Germany) in accordance with ASTM D150-11, "Standard Test Methods for AC Loss Characteristics and Permittivity (Dielectric Constant) of Solid Electrical Insulation." The parallel plate electrode configuration was selected for this measurement. The sample cell of parallel plates, an Agilent 16452A liquid test fixture consisting of 38 mm diameter parallel plates (Keysight Technologies, Santa Rosa, CA, US) was interfaced to the Alpha-A mainframe while utilizing the ZG2 Dielectric/Impedance General Purpose Interface available from Novocontrol Technologies. Each sample was prepared between parallel plate electrodes with a spacing, d, (typically, d=1 mm) and the complex permittivity (dielectric constant and loss) were evaluated from the phase sensitive measurement of the electrodes voltage difference (Vs) and current (Is). Frequency domain measurements were carried out at discrete frequencies from 0.00001 Hz to 1 MHz. Impedances from 10 milliohms up to $1\times10^{14}$ ohms were measured up to a maximum of 4.2 volts AC. For this experiment, however, a fixed AC voltage of 1.0 volts was used. The DC conductivity (the inverse of volume resistivity) can also be extracted from an optimized broadband dielectric relaxation fit function that contains at least one term of the low frequency Havrrilak Negami dielectric relaxation function and one separate frequency dependent conductivity term.

The liquid dielectric breakdown strength measurements were performed in accordance with ASTM D877-87(1995), "Standard Test Method for Dielectric Breakdown Voltage of Insulating Liquids." Disk electrodes 25 mm in diameter, with 2.5 mm (0.10") spacing between the electrodes, were utilized with a Phenix Technologies Model LD 60 that is specifically designed for testing in the 7-60 kV, 60 Hz (higher voltage) breakdown range. For this experiment, a frequency of 60 Hz and a ramp rate of 500 volts per second were utilized, as is typical.

Kinematic viscosity was determined in accordance with ASTM D445-94e1 "Standard Test Method for Kinematic Viscosity of Transparent and Opaque Liquids (the Calculation of Dynamic Viscosity)", except the bath temperature was controlled to ±0.1° C., using a ViscoSystem AVS 350 viscosity timer (Schott Instruments GmbH, Hattenbergstraße 10 55122 Mainz Germany) and Hagenbach-corrected 545-03, 545-13 or 545-20 Ubbelohde viscometers (Cannon Instruments Company, Box 812, State College, PA). For temperatures below 0° C., a Lawler temperature control bath was used.

Density was measured using DDM 2911 plus Automatic Density Meter. Before measurement, the fluid was briefly degassed in the syringe by stoppering the syringe tip and pulling on the plunger to release bubbles.

Flash points were measured according to the procedures outlined in ASTM D-3278-96 e-1 "Standard Test Methods for Flash Point of Liquids by Small Scale Closed-Cup Apparatus." Materials that demonstrated no flash point were considered to be non-flammable according to the ASTM test method.

Values of Log $K_{OW}$ (octanol/water partition coefficients) were determined by HPLC using the method described in Organization for Economic Cooperation and Development (OECD) Test Method 117, "Partition Coefficient (n-octanol/water), HPLC Method."

The atmospheric lifetime of each test material was determined from relative rate studies utilizing chloromethane ($CH_3Cl$) as a reference compound. The pseudo-first order reaction rates of the reference compound and the test compound with hydroxyl radicals (·OH) was determined in a laboratory chamber system. The atmospheric lifetime of the reference compound is documented in the literature. Based on this value and the pseudo-first order rates measured in the chamber experiments, the atmospheric lifetime for each specimen was calculated from the reaction rates for the test compound relative to the reference compounds and the reported lifetime of the reference compounds as shown below:

$$\tau_x = \tau_r \cdot \frac{k_r}{k_x}$$

where $\tau_x$ is the atmospheric lifetime of test material, $\tau_r$ is the atmospheric lifetime of the reference compound, and $k_x$ and $k_r$ are the rate constants for the reaction of hydroxyl radical with test material and the reference compound, respectively. The concentrations of gases in the test chamber were quantified by Fourier transform infrared spectroscopy (FTIR). The measured atmospheric lifetime value of each fluid was subsequently used for the GWP calculation.

Global Warming Potential (GWP) values were calculated using methods described in the Intergovernmental Panel on Climate Change (IPCC) Fifth Assessment Report (AR5). A gas standard of the material to be assessed, having a known and documented concentration, was prepared and used to obtain quantitative FTIR spectra of this compound. Quantitative gas phase, single component FTIR library reference spectra were generated at two different concentration levels by diluting the sample standard with nitrogen using mass flow controllers. The flow rates were measured using certified BIOS DRYCAL flow meters (Mesa Labs, Butler, NJ, US) at the FTIR cell exhaust. The dilution procedure was also verified using a certified ethylene calibration gas cylinder. Using methods described in AR5, the FTIR data were used to calculate the radiative efficiency, which in turn was combined with the atmospheric lifetime to calculate the GWP value.

Results

The properties of Examples 1-3 and Comparative Examples CE1-CE3 are summarized in Table 1. Examples 1 and 2, with a single chlorine atom attached to aromatic ring, have boiling points at least 22° C. above their non-chlorinated analogs (CE1 and CE2). Example 3, with two chlorine atoms attached to the aromatic ring, has a boiling point 35° C. above its non-chlorinated analog (CE1). For comparison, the 4-fluoro analog CE3 has a boiling point only 5° C. higher than its non-chlorinated analog (CE1). Thus, partial chlorination of the aromatic ring markedly increases the boiling point compared to non-chlorinated compounds, which enables higher temperature applications.

Replacing aromatic hydrogen atoms with chlorine atoms also impacts the dielectric properties. The compounds with a chlorine atom in the 4-position of the aromatic ring (Examples 1 and 2) or two chlorine atoms in the 3,5-positions (Example 3) exhibit significantly lower dielectric constants relative to non-chlorinated cases (CE1 and CE2). Further, the dielectric strength of Example 1 (46.6 kV) is considerably greater than its non-chlorinated analog, CE1, its 4-fluoro analog, CE3 (both 38.1 kV), and most commercial fluorinated fluids with comparable boiling points (e.g., 170-270° C.), such as hydrofluoroethers (<30 kV), perfluoropolyethers (~40 kV) and perfluorotrialkylamines (≤42 kV). Thus, the inclusion of even a single chlorine atom on the aromatic ring has surprisingly pronounced effects on dielectric properties, as illustrated by the data in Table 1. Interestingly, these effects are more prominent for chlorine than for fluorine, based on comparison of Example 1 with its 4-fluoro analog, CE3.

As shown in Table 1, Example 1 also had a very low global warming potential (<10).

TABLE 1

Properties of Examples 1-3 and Comparative Examples CE1-CE3.

| | Molecular Weight (g/mol) | Boiling Point (° C.) | Dielectric Constant @ 1 kHz | Dielectric strength (kV, 2.5 mm gap) | Viscosity at 0° C. (cSt) | Density at 25° C. ($g/cm^3$) | Flash Point (° C.) | Atm Lifetime (yrs) | GWP (100 yrs) | Log Kow |
|---|---|---|---|---|---|---|---|---|---|---|
| Ex. 1 | 558.6 | 223 | 2.57 | 46.6 | 24.1 | 1.65 | None | <0.3 | <10 | >6.4 |
| Ex. 2 | 408.6 | 193 | 2.76 | 50.7 | 8.4 | 1.58 | None | — | — | — |
| Ex. 3 | 593.1 | 237 | 2.54 | — | 40.8 | 1.70 | None | — | — | — |
| CE1 | 524.2 | 201 | 4.42 | 38.1 | 8.7 | 1.62 | None | 0.16 | <4 | >6.4 |
| CE2 | 374.0 | 169 | 5.16 | 31.1 | 3.6 | 1.51 | None | 0.27 | 11 | 5.5 |
| CE3 | 542.2 | 206 | 2.63 | 38.1 | 11.8 | 1.68 | None | — | — | >6.4 |

To evaluate thermal stability, a flame-sealed borosilicate glass tube (50 mm outer diameter, 0.4 mm wall thickness) containing Example 1 [1.0 g, isomeric mixture of 4-Cl $(C_6H_4)O(C_9F_{17})$] was completely submerged in a temperature-controlled oil bath at 200±2° C. for 31.5 days. After heating, there was no pressure build-up in the tube, indicating an absence of significant gaseous decomposition products. GC-FID data was collected after heating, which showed no evidence for decomposition or change in isomeric distribution [99.9±0.1% 4-Cl$(C_6H_4)O(C_9F_{17})$ isomers by GC-FID, before and after heating].

Thus, the chlorinated fluoroaromatic materials of the present invention are well suited for immersion cooling applications, by virtue of their high boiling points, excellent thermal stability, low dielectric constants, high dielectric strengths, and reduced environmental footprint.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows. All references cited in this disclosure are herein incorporated by reference in their entirety.

What is claimed is:

1. A chlorinated fluoroaromatic compound having structural formula (I):

I

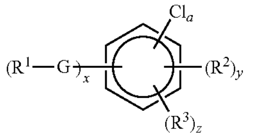

where G is an oxygen or sulfur atom;

each $R^1$ is, independently, a perfluorinated fluoroalkenyl group having 4 to 9 carbon atoms and optionally comprises one or more catenated heteroatoms;

each $R^2$ is, a hydrogen atom;

$R^3$ is a hydrogen atom;

a is 1;

x is 1 or 2;

y is 1-4; and z=6-a-x-y.

2. A chlorinated fluoroaromatic compound having structural formula (II):

II

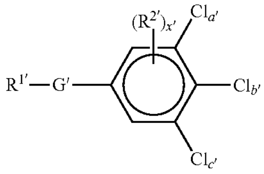

where G' is an oxygen or sulfur atom;

$R^{1'}$ is a perfluorinated fluoroalkenyl group having 4-9 carbon atoms and optionally comprises one or more catenated heteroatoms;

each $R^{2'}$ is, a hydrogen atom;

x' is 2-4; and a', b' and c' are, independently, 0 or 1, wherein if b' is 1, a' and c' are 0, and if b' is 0, a' and c; are 1.

3. An apparatus for heat transfer comprising:

a device; and a mechanism for transferring heat to or from the device, the mechanism comprising a working fluid that comprises the chlorinated fluoroaromatic compound of claim 1.

4. The apparatus for heat transfer of claim 3, wherein the device is selected from a microprocessor, a semiconductor wafer used to manufacture a semiconductor device, a power control semiconductor, an electrochemical cell, a battery pack, an electrical distribution switch gear, a power transformer, a circuit board, a multi-chip module, a packaged or unpackaged semiconductor device, a fuel cell, and a laser.

5. The apparatus for heat transfer of claim 3, wherein the mechanism for transferring heat is a component in a system for maintaining a temperature or temperature range of the device.

6. A method of transferring heat comprising:

providing a device; and transferring heat to or from the device using a heat transfer fluid that comprises the chlorinated fluoroaromatic compound of claim 1.

7. An immersion cooling system comprising:

a housing having an interior space;

a heat-generating component disposed within the interior space; and a working fluid liquid disposed within the interior space such that the heat-generating component is in contact with the working fluid liquid;

wherein the working fluid comprises the chlorinated fluoroaromatic compound of claim 1.

8. The immersion cooling system according to claim 7, wherein the chlorinated fluoroaromatic compound is present in the working fluid at an amount of at least 25% by weight based on the total weight of the working fluid.

9. The system according to claim 7, wherein the heat-generating component comprises an electronic device.

10. The system according to claim 9, wherein the electronic device comprises a computer server.

11. A thermal management system for a lithium-ion battery pack comprising:

a lithium-ion battery pack; and a working fluid in thermal communication with the lithium-ion battery pack;

wherein the working fluid comprises the chlorinated fluoroaromatic compound of claim 1.

* * * * *